United States Patent [19]

Remy

[11] 4,042,584

[45] Aug. 16, 1977

[54] ETHYNYLARYL PHENYL CYCLOPROPYL THIAZINES AND MORPHOLINES

[75] Inventor: David C. Remy, North Wales, Pa.

[73] Assignee: Merck & Co., Inc., Rahway, N.J.

[21] Appl. No.: 566,584

[22] Filed: Apr. 8, 1975

Related U.S. Application Data

[62] Division of Ser. No. 498,829, Aug. 19, 1974, Pat. No. 3,903,165.

[51] Int. Cl.$^2$ .......................................... C07D 295/02
[52] U.S. Cl. ..................................... 544/59; 424/246; 424/248.4; 424/248.58; 544/174; 544/178; 544/107; 544/110; 544/106
[58] Field of Search ............................ 260/243 B, 247

[56] References Cited

U.S. PATENT DOCUMENTS

| | | | |
|---|---|---|---|
| 3,719,712 | 3/1973 | Remy | 260/570.9 |
| 3,852,364 | 12/1974 | Diamond | 260/649 R |
| 3,882,130 | 5/1975 | Remy | 260/570.9 |
| 3,903,165 | 9/1975 | Remy | 260/570.5 CA |

*Primary Examiner*—Leonard Schenkman
*Attorney, Agent, or Firm*—Daniel T. Szura; J. Jerome Behan

[57] ABSTRACT

This application discloses arylethynylphenylcyclopropylamines and processes for their preparation. These amines exhibit monoamine oxidase (MAO) inhibiting activity.

6 Claims, No Drawings

ETHYNYLARYL PHENYL CYCLOPROPYL THIAZINES AND MORPHOLINES

This is a division of application Ser. No. 498,829 filed Aug. 19, 1974 now U.S. Pat. No. 3,903,165, issued Sept. 2, 1975.

BACKGROUND OF THE INVENTION

This invention relates to arylethynylarylcyclopropylamines, their method of preparation and pharmaceutical use.

Arylethynylaralkylamines of the general formula

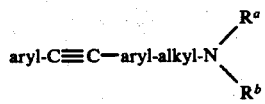

where alkyl is linear or branched hydrocarbyl and/or $R^a$ and $R^b$ are hydrogen or other substituents are disclosed in U.S. Pat. No. 3,719,712 and pending U.S. application Ser. No. 216,264 now U.S. Pat. No. 3,822,130. This class of compounds exhibits substantial anti-arrhythmic activity.

The present invention concerns novel cyclopropylamines having the general formyla

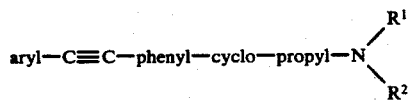

where $R^1$ and $R^2$ are hydrogen or other substituents. These novel compounds have activity as monoamine oxidase inhibitors. Inhibition of monoamine oxidase is an activity useful in the treatment of metal depression.

SUMMARY OF THE INVENTION

Compounds having the formula:

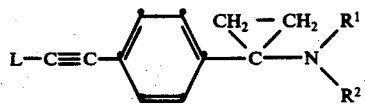

wherein L is aryl, preferably phenyl and $R^1$ and $R^2$ are various substituents, preferably hydrogen; and nontoxic pharmaceutically acceptable salts thereof; methods for preparing these compounds, and use as monoamine oxidase inhibitors.

DESCRIPTION OF THE PREFERRED EMBODIMENTS

The present invention is embodied broadly in compounds which are 1,2-diaryl derivatives of acetylene wherein one of the aryl substituents is an aromatic ring having at least one of its hydrogens replaced by an aminocyclopropyl radical, and in which the other aryl substituent includes unsubstituted homocyclic or heterocyclic aryl groups and substituted homocyclic and heterocyclic aryl groups.

A preferred class of compounds of the present invention are subbstituted cyclopropylamines have the formula:

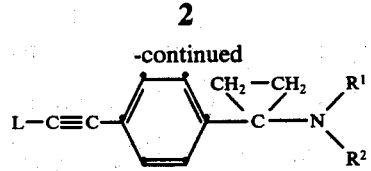

(I)

wherein L is aryl, and $R^1$ and $R^2$ (1) when separate, are independently selected from hydrogen, alkyl and alkenyl, cycloalkyl, perfluoroalkyl, aryl, acyl, and formyl, and (2) when joined are a 5-6 membered heterocyclic group.

Formula I compounds includes those in which L is biphenylyl, napthyl, indanyl, indenyl, phenyl or substituted phenyl having one or more, preferably one to three substituents selected from the group consisting of an alkyl having up to 6 carbon atoms, an alkenyl group having up to 6 carbon atoms, a perfluoroalkyl group having up to 4 carbon atoms, a phenyl or a substituted phenyl radical, a dialkylamino group having up to 8 carbon atoms, an alkylsulfonylamino group having up to 4 carbon atoms, hydroxyl, an alkoxyl group having up to 4 carbon atoms, mercapto, an alkylmercapto group having up to 4 carbon atoms or a halogen such as fluoro, chloro, bromo or iodo and $R^1$ and $R^2$ are separate.

An especially preferred group of compounds of the invention are those having the formula:

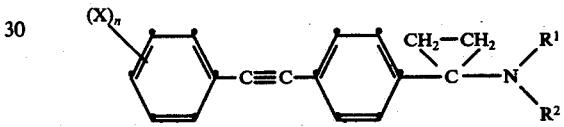

wherein X is selected from halogen, including Cl, I Br and F, hydrogen, lower alkoxy of 1–4 carbons, preferably methoxy, lower alkyl of from 1–4 carbons, preferably methyl, hydroxy, phenyl, alkyl, mercapto, alkyl sulfonyl, sulfamoyl, and trifluoromethyl; n is 1 or 2 and $R^1$ and $R^2$ are independently selected from hydrogen and lower alkyl substituents having from 1 to 6 carbon atoms, preferably 1 to 4 carbon atoms, and methyl most preferably; and pharmaceutically acceptable salts thereof.

Still more preferred compounds of the present invention are those having the formula:

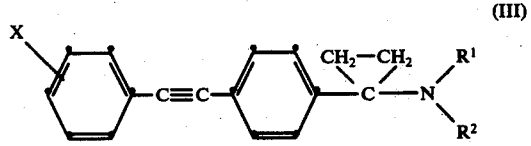

(III)

wherein X is selected from halogen including Cl, F I and Br, —$CF_3$, $C_1$-$C_4$ alkyl, $C_1$-$C_4$ alkoxy, and phenyl and $R^1$ and $R^2$ are independently selected from hydrogen and $C_1$-$C_3$ alkyl; and pharmaceutically acceptable salts thereof. Most preferred compounds are 1-[4-(phenylethynyl)phenyl]cyclopropylamine having the formula:

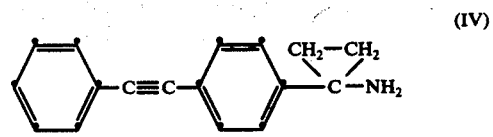

(IV)

and non-toxic, pharmaceutically acceptable salts thereof.
Illustrative of the compounds of the present invention are
1-[4-(biphenylylethynyl)phenyl]cyclopropylamine;
1-[4-(p-tolylethynyl)phenyl]cyclopropylamine;
1-[4-(2-methoxyphenylethynyl)phenyl]cyclopropyl-N-methylamine;
1-[4-(3-fluorophenylethynyl)phenyl]cyclopropylmorpholine
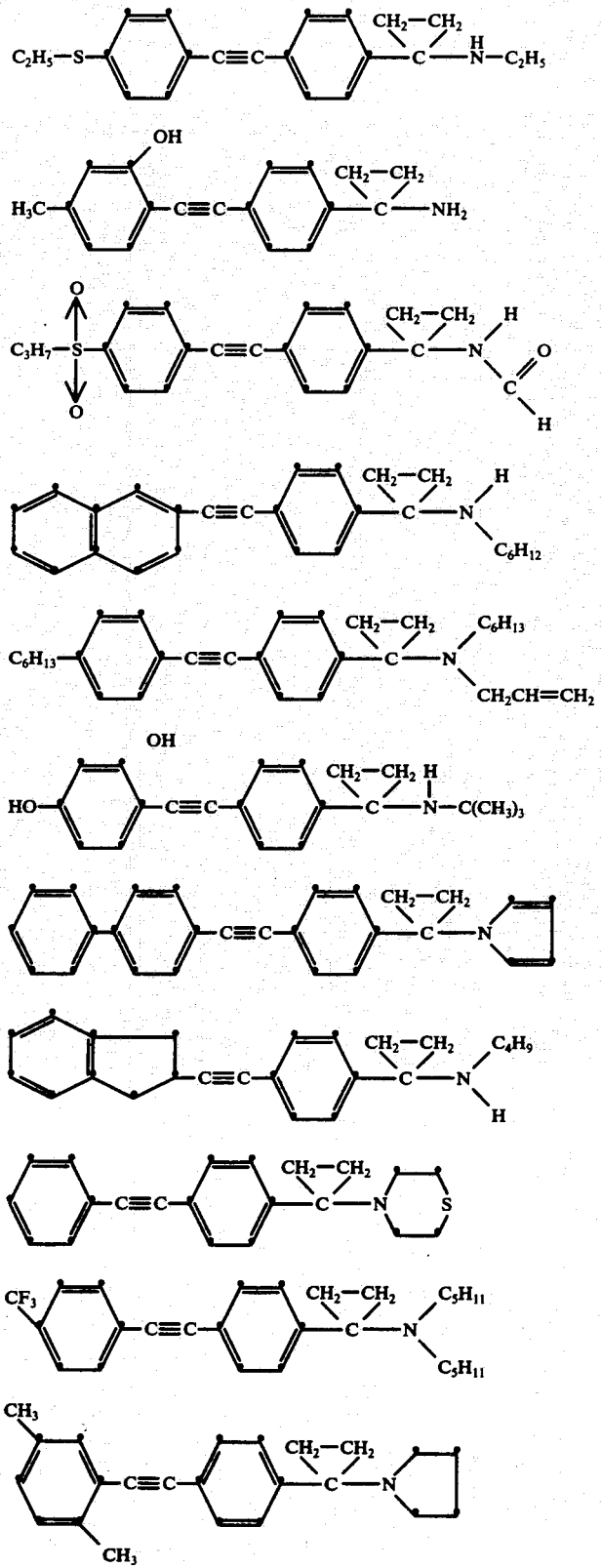

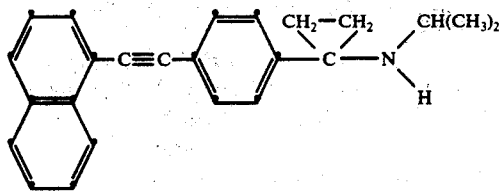

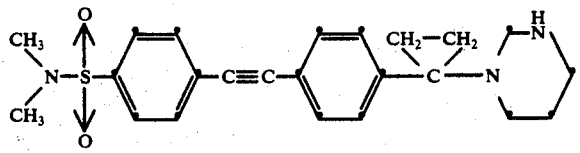

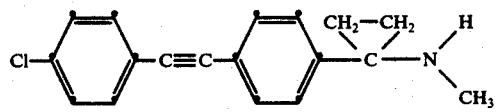

1-[4-(phenylethynyl)phenyl]cyclopropyl-N,N-di-t-butylamine;
1-[4-(3-iodophenylethynyl)phenyl]-cyclopropylamine; 1-[4-(3,5-dibromophenylethynyl)phenyl]cyclopropyl-N-propylamine; 1-[4-(4-cyclohexylphenylethynyl)phenyl]cyclopropyl-N-cyclopropylamine; 1-[4-(phenylethynyl)phenyl]cyclopropyl-N-hexylamine and the like; and their non-toxic pharmaceutically acceptable salts.

The non-toxic pharmaceutically acceptable salts of the present amines are generally the acid addition salts. They are prepared by reacting the amine compound with sufficient acid to neutralize at least one, and preferably all the basic nitrogens in said amine. Useful salts are those of the present cyclopropyl amine and an inorganic acid or an organic acid. Useful inorganic acids are the hydrohalo acids such as HCl and HBr, sulfuric acid, phosphoric acid, and the like. Useful organic acids are those such as sorbic acid, citric acid, malic acid, maleic acid, tartaric acid, lactic acid, propionic acid, succinic acid, adipic acid and the like Examples of useful salts are 1-[4-(phenylethynyl)phenyl]cyclopropylamine hydrochloride 1-[4-(p-tolylethynyl)phenyl]cyclopropyl-N-methylamine hydrogen maleate 1-[4-(o-bromophenylethynyl)phenyl]cyclopropylamine succinate 1-[4-(β-naphthylethynyl)phenyl]cyclopropyl-N-amyl dihydrogenphosphate
and the like.

REACTION SEQUENCE A

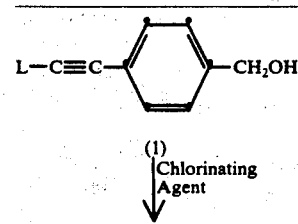

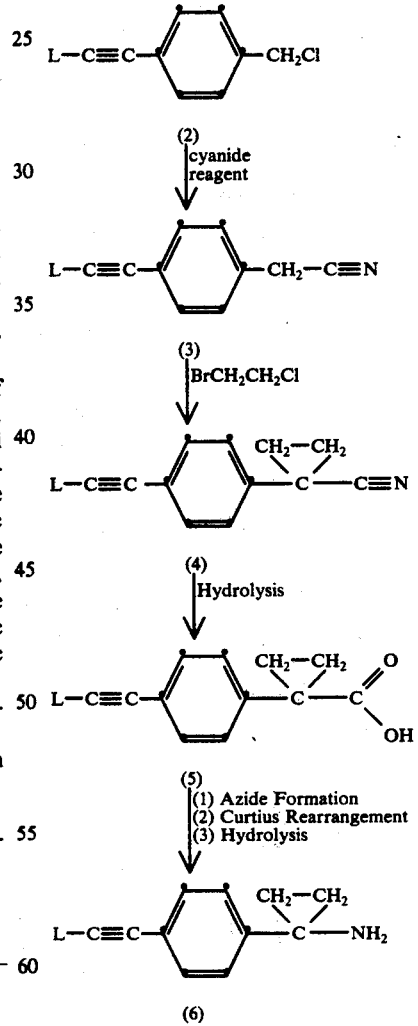

The final product (6) can be converted to corresponding N-substituted or N,N-disubstituted compounds by any applicable reaction.

The following example illustrates, but does not limit, the process of Sequence A.

EXAMPLE 1

A. 4-(Phenylethynyl)phenylacetonitrile

To a solution of 6.0 g. (0.0288 mole) of 4-phenylethynyl)benzyl alcohol in 100 ml. of chloroform is added dropwise 7 ml. of thionyl chloride. The solution is stirred at room temperature for 6 hours. Evaporation of the solvents leaves a solid that is sublimed at 65° (0.05 mm.) to give 6.0 g. (92%) of 4-(phenylethynyl)benzyl chloride, m.p. 61.5°–63.5°.

Anal. Calcd. for $C_{15}H_{11}Cl$: C, 79.47; H, 4.89. Found: C, 79.60; H 4.98.

A mixture of 3.72 g. (0.076 mole) of sodium cyanide in 30 ml. of dry dimethylsulfoxide is heated to 90°–95°. On cooling to 35°, the mixture forms a gelatinous mass that is stirred manually while 8.0 g. (0.0354 mole) of the above chloride is added. The mixture is stirred overnight and is poured into 400 ml. of water. The precipitate is collected, dissolved in benzene, washed with water, dried over magnesium sulfate, and the solvent removed. The residue is recrystallized from cyclohexane to yield 13.25 g. (88%) of 4-(phenylethynyl)phenylacetonitrile, m.p. 76°–70°. An analytical sample is prepared by sublimation at 80° (0.05 mm), m.p. 78-80°.

Anal. Calcd. for $C_{16}H_{11}N$:C, 88.45; H,5.10; N,6.45. Found: C,88.67; H,5.10; N, 6.31.

1-[4-(Phenylethynyl)phenyl]cyclopropane carbonitrile

Sodamide, prepared from 0.46 g. (0.02 g. - atom) of sodium and suspended in 10 ml. of ether, is stirred at room temperature while a solution of 2.17 g. (0.01 mole) of 4-(phenylethynyl)phenylacetonitrile in 15 ml. of ether is added dropwise. The mixture is refluxed for 4 hours, and then is cooled in an ice-salt bath while a solution of 1.43 g. (0.01 mole) of 1-bromo-2-chloroethane in 2 ml. of ether is added dropwise. The mixture is stirred overnignht at room temperature, refluxed for 4 hours, cooled, and diluted with 20 ml. of water. The aqueous phase is separated, re-extracted with ether, and the combined organic phases are washed with water and dried over magnesium sulfate. The oily solid residue obtained by exaporation of the ether is freed from oil by trituration with ether and sublimed at 80° (0.05 mm) to yield to 1.28 g. (53%) of 1-[4-(phenylethynyl)-phenyl]cyclopropane carbonitile, m.p. 93-95° C.

Anal. Calc'd for $C_{18}H_{13}N$:Cm 88.86; H, 5.39; N.576. Found: C, 88.99; H, 5.55; N, 5.52.

C. 1-[4-(Phenylethynyl)phenyl]cyclopropane carboxamide

A mixture of 3.49 g (0.014 mole) of 1-[4-phenylethynyl)phenyl]cyclopropane carbonitrile, 20 drops of 25% potassium hydroxide, 18 ml. of 30% hydrogen peroxide, and 140 ml. of methanol is heated at 55-60° for 8 hours, with additions of 10 ml. of 30% hydrogen peroxide and 10 drops of 25% potassium hydroxide after 4.5 hours and 5 ml. of 30% hydrogen peroxide after 6 hours. The product crystallization from benzene-cyclohexane gives pure 1-[4-(phenylethynyl)phenyl]cyclopropane carboxamide, m.p. 174°–175.5°.

Anal. Calc'd for $C_{17}H_{15}NO$:C, 82.73; H, 5.78; N,5.36. Found: C, 83.07; H, 5.91; N, 5.32.

D. 1-[4-(Phenylethynyl)phenyl]cyclopropane carboxylic acid

A mixture of 2.92 g. (0.0112 mole) of 1-[4-(phenylethynyl)phenyl]cyclopropane carboxamide, 90 ml. of methanol, 90 ml. of tetrahydrofuran, and 60 ml. of 10% sodium hydroxide is refluxed for 66 hours. After removing solvents, the sodium salt is collected and washed with water and methylene chloride. The precipitate is stirred in a mixture of 6N hydrochloric acid and methylene chloride until all the solid is dissolved. The organic phase is removed, washed with water, dried (MgSO₄), filtered, and the solvent removed to give 1.95 g. (66%) of 1-[4-(phenylethynyl)phenyl]cyclopropane carboxylic acid, m.p. 214°–218°. The product is recrystallized from benzene-cyclohexane, m.p. 215°–218°.

Anal. Calc'd. for $C_{18}H_{14}O_2$:C, 82.42; H, 5.38. Found: C, 82.36; H, 5.37.

E. 1-[4-(Phenylethynyl)phenyl]cyclopropylamine.

To a stirred suspension of 2.52 g. (0.0096 mole) of 1-[4-(phenylethynyl)phenyl]cyclopropane carboxylic acid in 12 ml. of acetone - 2 ml. of water, cooled in an ice-salt bath, is added dropwise a solution of 1.13 g. (0.0112 mole) of triethylamine in 9.5 ml. of acetone followed by a solution of 1.31 g. (0.012 mole) of ethyl chloroformate in 5.5 ml. of actone. After stirring for 0.5 hours, a solution of 0.94 g (0.0145 mole) of sodium azide in 3 ml. of water is added. After stirring for one hour, the mixture is poured into 80 ml. of water and the azide is extracted into toluene. The water washed and magnesium sulfate dried toluene extract is heated for 0.5 hour on a steam bath, evaporated to about 15 ml. and benzyl alcohol (2ml.) is added. The mixture is heated for 6 hours on the steam bath and if filtered hot. N-Benzyloxycarbonyl-1-[4-(phenylethynyl)phenyl]cyclopropylamine, 2.9 g. (82%) precipitated from the cooled filtrate. The material is recrystallized from benzene-hexane and from isopropyl alcohol, m.-. 171°–173°.

Anal. Calc'd. for $C_{25}H_{21}NO_2$: C, 81.72; H, 5.76; N, 3.81. Found: C, 81.72; H, 5.81; N, 3.76.

A solution of the above benzylurethane (1.0 g., 0.0027 mole) and 8 g. of potassium hydroxide in 40 ml. of n-butanol is heated at 115°–120° for 7 hours, cooled, and poured into 250 ml. or water. The aqueous layer is separated and extracted with benzene. The combined organic phases are washed with water and extracted with 0.5 M citric acid. Neutralization of the acid extract with 40% sodium hydroxide precipitated 0.51 g. (80%) of 1-[4-(phenylethynyl)phenyl]cyclopropylamine as white crystals, m.p. 112°–116°. The product is recrystallized from hexane, m.p. 117°–118°.

Anal. Calc'd. for $C_{17}H_{15}N$:C, 87.51; H, 6.48; N, 6.00. Found: C, 87.27; H, 6.44; N, 6.12.

Corresponding cyclopropylamines are prepared when the following benzyl alcohols are substituted for the 4-(phenylethynyl)benzyl alcohol in the Example 1 procedure:

4-(3-cyclohexylphenylethynyl)benzylalcohol,
4-(2,4-xylylethynyl) benzyl alcohol,
4-(4-t-butylphenylethynyl)benxyl alcohol,
4-(3-ethoxyphenylethynyl)benzyl alcohol, 4-(3,5-dibromophenylethynyl)benzyl alcohol
4-(3,5-dibromophenylethynyl)benzyl alcohol
4-(diphenylylethynyl)benzyl alcohol and the like.

The N-mono- and N,N-dialkyl substituted derivatives of these cyclopropylamines are prepared by availiable alkylation methods, e.g. treatment with formaldehyde and HCOOH or acylation of the amine followed by reduction.

Another method for preparing the present cycloalkylamines is illustrated by the following reaction sequence:

REACTION SEQUENCE B

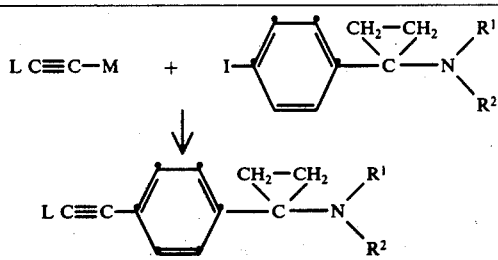

The reaction sequence utilizes an aryl metal acetylide and a suitable aryl iodide to prepare the amine compounds directly. M in the above equation may be Ag or Cu while L, $R^1$ and $R^2$ are as defined above. A most suitable acetylide is the cuprous acetylide

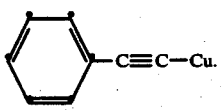

The compounds of the present invention, both the free amines and their pharmaceutically acceptable salts, are pharmacologically active in inhibiting monoamine oxidase. This activity was demonstrated by determining the effect of an amine of the present invention on brain serotonin. The following test procedure was used:

Female albino mice were given (interperitoneally) single dose of 1-[4-(phenylethynyl)phenyl]cyclopropylamine (150 mg./kg.). After 90 minutes, the mice were sacrificed and the brains were removed immediately. Five pools of four brains each from treated and untreated mice were assayed for serotonin by the general method described in J. Biol. Chem. 215, 337 (1955), with the single exception that three extractions with 25 ml. of heptane were carried out immediately prior to butanol extraction in order to remove interfering drug. The results of the test are tabulated below.

TABLE 1
Determination of MAO Inhibition by Serotonin Level

| Test | Animal Treatment | Serotonin Level ($\mu$/g) |
|---|---|---|
| 1 | none | 0.75 |
| 2 | 150 mg./kg. of Example 1 compound | 1.41 |

The data shows that the serotonin level of the mice treated with an amine of the present invention was substantially increased. Since inhibition of monoamine oxidase is known to effect an increase in serotonin level, the data in Table 1 clearly indicates that the Example 1 compound is a monoamine oxidase inhibitor.

In addition to the in vivo MAO inhibition demonstrated by the Example 1 compound, comparable in vitro MAO inhibition by the Example 1 compound was also observed.

Analogous MAO inhibition is effected by any of the cyclopropylamines (and/or salts thereof) disclosed herein.

Since it is recognized that an increase in serotonin level by MAO inhibition stimulates the central nervous system, MAO inhibitors have found use in treatment of patients suffering from mental depression. The amount of MAO inhibitor compounds to be used in treating mental depression will vary, depending on the severity of the depression, the physical condition of the patient, the relative activity of the compound used, the mode of administration and other factors. Generally, daily doses ranging from 0.01 to 15 mg. per kilograms can be used. The compounds of the present invention can be administered by any suitable mode such as orally, intravenously, intraperitoneally etc. Suitable dosage forms are used depending on the mode of administration. The compounds of the present invention can be administered as the free amines or preferably as pharmaceutically acceptable salts. For oral administration, the compounds can be used in tablets, capsules, microcapsules, in palatable liquid carriers and the like. For administration by injection, the compounds can be conveniently dissolved or dispersed in a pharmaceutically acceptable carrier.

Claims to the invention follow.

What is claimed is:

1. A compound selected from the group consisting of
    a. a substituted cyclopropylamine having the formula

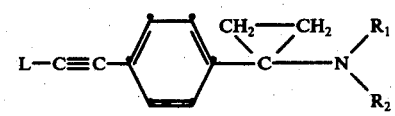

wherein L is selected from the group consisting of phenyl and

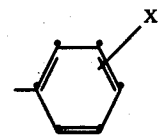

wherein X is Cl, Br, I, F, $-CF_3$, $-C_1-C_4$alkyl, $-C_1-C_4$ alkoxy or phenyl and $R_1$ and $R_2$ are joined forming a

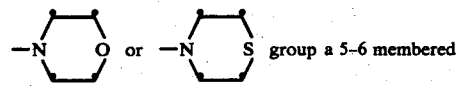

and b. a non-toxic, pharmaceutically acceptable salt of (a).

2. The compound of claim 1 wherein L is said

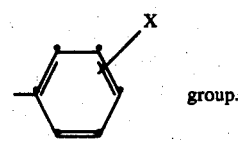

group.

3. The compound of claim 1 wherein L is phenyl.

4. The compound of claim 2 wherein said heterocyclic group is morpholino or 1,4-tetrahydrothiazinyl.

5. The compound of claim 1 wherein L is 3-fluorophenyl and said heterocyclic group is morpholino.

6. The compound of claim 1 wherein L is phenyl and said heterocyclic group is 1,4-tetrahydrothiazinyl.

* * * * *

UNITED STATES PATENT AND TRADEMARK OFFICE
CERTIFICATE OF CORRECTION

PATENT NO. : 4,042,584
DATED : August 16, 1977
INVENTOR(S) : David C. Remy

It is certified that error appears in the above-identified patent and that said Letters Patent are hereby corrected as shown below:

In Claim 1., column 10, line 45

" 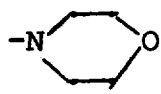 or  group a 5-6 membered "

should read

--- 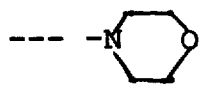 or 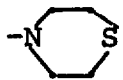 group ---

Signed and Sealed this

First Day of November 1977

[SEAL]

Attest:

RUTH C. MASON
Attesting Officer

LUTRELLE F. PARKER
Acting Commissioner of Patents and Trademarks